United States Patent [19]

Pauling et al.

[11] Patent Number: 4,997,958

[45] Date of Patent: Mar. 5, 1991

[54] PROCESS FOR PRODUCING ASCORBIC ACID 6-ESTERS

[75] Inventors: Horst Pauling, Bottmingen; Christof Wehrli, Witterswil, both of Switzerland

[73] Assignee: Hoffmann-La Roche Inc., Nutley, N.J.

[21] Appl. No.: 321,948

[22] Filed: Mar. 10, 1989

Related U.S. Application Data

[62] Division of Ser. No. 207,422, Jun. 16, 1988, abandoned.

[30] Foreign Application Priority Data

Jun. 26, 1987 [CH] Switzerland ............... 2431/87
Mar. 24, 1988 [CH] Switzerland ............... 1112/88

[51] Int. Cl.$^5$ ........................................... C07D 307/62
[52] U.S. Cl. ........................................ 549/315; 549/317
[58] Field of Search ................................ 549/315, 317

[56] References Cited

U.S. PATENT DOCUMENTS 2,454,748  11/1948  Weisblat et al. ............... 549/315
3,250,790   5/1966  Klaui ............................ 260/343.7

FOREIGN PATENT DOCUMENTS 1468406  12/1968  Fed. Rep. of Germany .
62-81307   4/1987  Japan .

OTHER PUBLICATIONS

Kanebo, Derwent 87-14094/20 (1987).
Taisho, Derwent 9530 (1963).

Primary Examiner—Frederick E. Waddell
Assistant Examiner—Ba K. Trinh
Attorney, Agent, or Firm—George M. Gould; Bernard S. Leon; Alan P. Kass

[57] ABSTRACT

A process for the manufacture of 6-aliphatic $C_{2-20}$-carboxylic acid esters of ascorbic acid by esterifying the ascorbic acid with an aliphatic $C_{2-20}$-carboxylic acid halide in the presence of a N,N-dialkyl-alkanecarboxylic acid amide, of a cyclic amide of the 1-methyl-2-pyrrolidone type, of a tetraalkylcarbamide such as tetramethylurea, of a cyclic carbamide of the 1,3-dimethyl-2-imidazolidinone type or of a phosphoric acid triamide of the hexamethylphosphoric acid triamide type. The 6-ascorbyl linolate which can be manufactured in this manner is novel and is likewise an object of the present invention. The thus-manufacturable 6-aliphatic $C_{2-20}$-carboxylic acid esters of ascorbic acid are important alternative application forms of L-ascorbic acid (vitamin C).

14 Claims, No Drawings

PROCESS FOR PRODUCING ASCORBIC ACID 6-ESTERS

This is a division of application Ser. No. 07/207,422 filed, Jun. 16, 1988, now abandoned.

BACKGROUND OF THE INVENTION

1. Field of the Invention

The present invention is concerned with a novel process for the manufacture of ascorbic acid 6-esters which are important alternative application forms of L-ascorbic acid (vitamin C).

2. Description

Vitamin C is known not only as an additive to foodstuffs for human beings and animals, but also as an antioxidant, especially for fats and oils. In contrast to vitamin C itself, the vitamin C esters are oil-soluble, which leads, for example, to an increased efficacy as antioxidants.

SUMMARY OF THE INVENTION

The present invention provides a process which enables ascorbic acid 6-esters to be manufactured in a simple and inexpensive manner, with the particular desired ascorbic acid 6-ester being obtained in high yield and in good quality. In accordance with the invention, 6-aliphatic $C_{2-20}$-carboxylic acid esters of ascorbic acid are produced by esterifying ascorbic acid with an aliphatic $C_{2-20}$-carboxylic acid halide and carrying out the esterification in the presence of a N,N-dialkyl-alkanecarboxylic acid amide of the formula

$$R^1\text{—}CONR^2R^3 \quad \text{I}$$

or of a cyclic amide of the formula

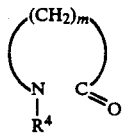

II or of a tetraalkylcarbamide of the formula

$$R^5R^6NCONR^7R^8 \quad \text{III}$$

or of a cyclic carbamide of formula

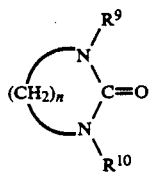

IV wherein $R^1$ signifies straight-chain or branched $C_{1-5}$-alkyl; $R^2$, $R^3$, $R^4$, $R^5$, $R^6$, $R^7$, $R^8$, $R^9$ and $R^{10}$ each signify methyl or ethyl; m signifies 3, 4 or 5 and n signifies 2, 3 or 4, or a phosphoric acid triamide of the formula

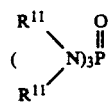

V wherein $R^{11}$ signifies methyl or ethyl or the two $R^{11}$ symbols together with the nitrogen atom to which they are attached signify piperidino.

DETAILED DESCRIPTION OF THE INVENTION

The present invention is directed to a process for producing 6-aliphatic $C_{2-20}$-carboxylic acid esters of ascorbic acid. In accordance with the inventive process, ascorbic acid is esterified with an aliphatic $C_{2-20}$-carboxylic acid halide in the presence of one or more of the amides of formula I-V, described above.

Under "ascorbic acid" there are to be understood especially L-ascorbic acid and its enantiomer, as well as D-erythorbic acid and its enantiomer. The 6-aliphatic $C_{2-20}$-carboxylic acid esters of ascorbic acid as well as the aliphatic $C_{2-20}$-carboxylic acid halides likewise mentioned above have, depending on the number of carbon atoms, a saturated or (singly or multiply) unsaturated, straight-chain or branched aliphatic acyl group.

The term "acyl" denotes a radical derived from a carboxylic acid and having the formula:

wherein R is branched or straight-chain $C_{1-19}$ alkyl or branched or straight-chain $C_{2-19}$ alkenyl.

Examples of respective saturated, straight-chain or branched acyl groups are acetyl, propionyl, butyryl, pivaloyl, decanoyl, myristoyl, palmitoyl and stearoyl, while oleoyl and linoloyl are examples of unsaturated acyl groups.

The term "halide" or "halo" represents all forms thereof—chloride, bromide, iodide and fluoride unless otherwise stated.

The acid chlorides and acid bromides especially come into consideration as aliphatic $C_{2-20}$-carboxylic acid halides. Palmitoyl chloride and linoloyl chloride are preferred aliphatic $C_{2-20}$-carboxylic acid halides which can be used in the process in accordance with the invention. Preferably, L-ascorbic acid is esterified in accordance with the invention using these acid chlorides.

Among the substances (solvents) which can be used in accordance with the invention and in the presence of which the esterification is carried out are the N,N-dialkylalkane-carboxylic acid amides of formula I, those cyclic amides of formula II in which $R^4$ signifies methyl, tetramethyl-urea (the tetraalkylcarbamide of formula III in which $R^5$, $R^6$, $R^7$ and $R^8$ each signify methyl), those cyclic carbamides of formula IV in which not only $R^9$ but also $R^{10}$ signifies methyl and hexamethylphosphoric acid triamide (the phosphoric acid triamide of formula V in which $R^{11}$ signifies methyl). These form an interesting group of such substances. N,N-Dimethylacetamide (an example of a N,N-dialkylalkanecarboxylic acid amide of formula I); 1-methyl-2-pyrrolidone (an example of a cyclic amide of formula II); tetramethylurea (an example of a tetraalkyl-carbamide of formula III); 1,3-dimethyl-3,4,5,6-tetrahydro-2(1H)-pyrimidinone and 1,3-dimethyl-2-imidazolidinone (examples of a cyclic carbamide of formula IV); and hexamethylphosphoric acid triamide (an example of a phosphoric acid triamide of formula V) are preferred, with N,N-dimethylacetamide and 1-methyl-2-pyrrolidone being especially preferred.

It has been found to be advantageous to use the ascorbic acid in up to 25 weight percent excess, especially in about 10 weight percent excess, based on the amount of acid halide. It has been found that the use of excess ascorbic acid prevents undesired multiple acylation, e.g. the formation of 5,6-ascorbyl dipalmitate when L-ascorbic acid is esterified with palmitoyl chloride.

In general, although temperature is not critical, the esterification is carried out at temperatures of about −20° C. to about 40° C., with the highest yields of product being obtained at reaction temperatures about 0° C. At too low reaction temperatures, however, the palmitoyl chloride has too low a solubility, so that a less than complete esterification can be expected. On the other hand, at too high temperatures increased by-products are formed.

Depending on the solvent which is used in accordance with the invention, the ascorbic acid is soluble in this up to about 35%, with the solutions of higher concentration being undesirably viscous. It has been found that an additional inert solvent can be used to decrease the viscosity of the reaction mixture without adversely influencing the course of the esterification. The presence of this additional solvent even confers advantages to the esterification, since thereby a higher yield of product can be obtained. Preferred additional inert solvents are halogenated (especially chlorinated) aliphatic hydrocarbons, especially methylene chloride and chloroform; cyclic ethers, especially tetrahydrofuran and dioxan, as well as acetonitrile. When the additional inert solvent is used, the volume ratio of the substance (solvent) used in accordance with the invention to the inert solvent is preferably about 1:0.1 to about 1:1, especially about 1:0.5.

Further, it has been found that the yield of product is substantially increased by the addition of a hydrohalide, especially of hydrogen chloride, to the reaction mixture, especially when N,N-dimethylacetamide, 1-methyl-2-pyrrolylidone, tetramethylurea, 1,3-dimethyl-3,4,5,6-tetrahydro-2(1H)-pyrimidinone or 1,3-dimethyl-2-imidazolidinone is used as the (main) solvent. Increasing yields of product are obtained by increasing the addition of hydrogen halide up to a molar ratio of ascorbic acid to hydrogen halide of about 1:2, especially in the range of about 1:0.1 to about 1:2. This ratio is about 1:1 in an especially preferred embodiment.

The ascorbic acid 6-esters produced in accordance with the invention can be isolated and purified according to known methods. Preferably, for example, in the case of the manufacture of 6-ascorbyl palmitate the reaction mixture after completion of the esterification is diluted with water as well as a suitable organic solvent, especially diethyl ether, diisopropyl ether, ethyl acetate or isobutyl methyl ketone, and the resulting 6-ascorbyl palmitate is filtered off in crystalline form from the diluted reaction mixture. After the filtration and subsequent drying the thus-isolated 6-ascorbyl palmitate is normally present as a white crystallizate which requires no further purification, since any byproducts, e.g. small amounts of 5-ascorbyl palmitate and 5,6-ascorbyl dipalmitate, remain behind in the filtrate. The solvent used in the esterification, e.g. dimethylacetamide, can be recovered in good yield from the aqueous filtrate in a conventional manner, e.g. distillation or extraction, and can be recyclized, which represents a further advantage of the process in accordance with the invention.

In contrast to the 6-ascorbyl palmitate, the 6-ascorbyl linolate, for example, is manufactured in non-crystalline form. The majority of the polar and non-polar impurities as well as byproducts can be removed by distribution extraction. When, which is normally the case, the linoloyl halide used in accordance with the invention is derived from a linolic acid of technical quality, which consists of a mixture of about 60% linolic acid, 30% oleic acid as well as further unsaturated fatty acids, the 6-ascorbyl linolate manufactured therewith likewise consists of a product mixture which reflects the composition of the linolic acid used. When pure linolic acid is used, there is obtained correspondingly pure linolate.

The 6-ascorbyl linolate manufactured in accordance with the invention is novel and forms a further object of the present invention. Due to its surprising high solubility in fats 6-ascorbyl linolate is an especially interesting antioxidant which is well suited, for example, for the antioxidative stabilization of vegetable oils.

The process in accordance with the invention is illustrated further by the following Examples. Temperatures are in degrees Celsius, and room temperature is about 20° C. The Examples were carried out as written.

EXAMPLE 1

6-ascorbyl palmitate 26.5 ml of N,N-dimethylacetamide are placed at 0° C. in a reaction vessel provided with a thermometer, gas inlet tube, stirrer and dropping funnel. 2.0 g (55 mmol) of hydrogen chloride gas are then introduced at 10° C. and 9.69 g (55 mmol) of crystalline L-ascorbic acid and 13.25 ml of methylene chloride area added. 15.2 ml (50 mmol) of palmitoyl chloride are added dropwise to the resulting clear solution at 0° C. within 4 hours. The reaction mixture is stirred at 0° C. for 18 hours and subsequently at 20° C. for 30 minutes.

100 ml of ethyl acetate (alternatively there can be used, inter alia, diethyl ether, diisopropyl ether or isobutyl methyl ketone) and 200 ml of water are then added to the reaction mixture. The aqueous mixture is stirred at 0° C. for 2 hours. The crystallized-out product is subsequently filtered off under suction at 0° C. the filter cake is worked up thoroughly into a paste three times with 50 ml of water each time and rinsed. Finally, the well-dried suction-filtered crystallizate is dried up to constant weight at 50° C. for 18 hours in a water-jet vacuum.

In this manner there is obtained 6-ascorbyl palmitate (17.97 g, which corresponds to a theoretical yield of 86.7%), m.p 112°–113° C.; $[\alpha]_D^{20}+21.1$ (1% ethanol); purity according to high pressure liquid chromatography 99%.

EXAMPLE 2

The procedure described in Example 1 is carried out analogously using N-methyl-2-pyrrolidone as the solvent in place of N,N-dimethylacetamide. In this manner there are obtained 17.30 g of 6-ascorbyl palmitate (83.5% of the theoretical yield), m.p 112°–113° C.; $[\alpha]_D^{20} = +21.3$ (1% ethanol); purity according to high pressure liquid chromatography 99%.

EXAMPLE 3

The procedure described in Example 1 is carried out analogously using hexamethylphosphoric acid triamide and tetrahydrofuran as the solvents in place of N,N-dimethylacetamide and methylene chloride. In this manner there are obtained 17.80 g of 6-ascorbyl palmitate (86.0% of the theoretical yield), m.p. 112°–113° C.;

purity according to high pressure liquid chromatography 99%.

EXAMPLE 4

6-ascorbyl linolate 59.2 g (211 mmol) of linolic acid (technical quality: consisting of about 55% linolic acid, 35% oleic acid and further unsaturated fatty acids), 60 ml of toluene and 17 ml (234 mmol) of thionyl chloride are combined under a protective gas in a reaction vessel provided with a thermometer, magnetic stirrer, dropping funnel, reflux condenser and gas-washing bottles. 0.5 ml of dimethylformamide is added to the mixture as the catalyst and the whole is then stirred at room temperature for about 18 hours, until the evolution of gas (sulphur dioxide, hydrogen chloride) has finished. The resulting solution is concentrated at 45° C. on a rotary evaporator in a water-jet vacuum in order to remove excess thionyl chloride. 63.1 g of linoloyl chloride remain as the residue.

120 ml of N,N-dimethylacetamide are placed under a protective gas in a reaction vessel provided with a thermometer, gas inlet tube and stirrer, 8.8 g (240 mmol) of hydrogen chloride gas are then introduced at 10° C. and 42.3 g (240 mmol) of crystalline L-ascorbic acid and 60 ml of methylene chloride are added. 72.6 g (211 mmol) of linoloyl chloride are added dropwise to the resulting clear solution at 0° C. (ice-bath temperature) within 4 hours. The reaction mixture is stirred at 0° C. for 18 hours.

400 ml of water and 400 ml of diethyl ether are then added to the reaction mixture. The aqueous mixture is stirred for 10 minutes and subsequently extracted three times with 100 ml of diethyl ether each time. The organic phases are combined and dried over anhydrous sodium sulphate. The solution is concentrated at 40° C. on a rotary evaporator in a water-jet vacuum. Finally, the resulting solid residue is dried over phosphorus pentoxide up to constant weight for 18 hours at 30° C. in a water-jet vacuum. In this manner there is obtained 6-ascorbyl linolate (86.6 g, which corresponds to a theoretical yield of 93.6%) as a solid resin, $[\alpha]^{D20} + 17.4$ (1% ethanol).

We claim:

1. A process for producing 6-aliphatic $C_{2-20}$-carboxylic acid esters of ascorbic acid comprising esterifying ascorbic acid with an aliphatic $C_{2-20}$-carboxylic acid halide wherein there is an excess of the ascorbic acid to aliphatic $C_{2-20}$carboxylic acid halide, in the presence of (a) a N,N-dialkyl-alkanecarboxylic acid amide of the formula $$R^1\text{---}CONR^2R^3$$

I or of a cyclic amide of the formula

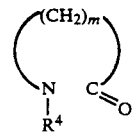

II wherein $R^1$ is straight-chain or branched $C_{1-5}$-alkyl; each of $R^2$, $R^3$ and $R^4$ individually is methyl or ethyl; and m is an integer 3, 4 or 5, and (b) a hydrogen halide to produce said esters of ascorbic acid.

2. The process of claim 1, wherein the esterification is carried out in the presence of the N,N-dialkyl-alkanecarboxylic acid amide of formula I or of the cyclic amide of formula II in which $R^4$ is methyl.

3. The process of to claim 1, wherein L-ascorbic acid is esterified.

4. The process of claim 1, wherein palmitoyl chloride or linoloyl chloride is used as the aliphatic $C_{2-20}$-carboxylic acid halide.

5. The process of claim 1, wherein the esterification is carried out in the presence of N,N-dimethyl-acetamide or 1-methyl-2-pyrrolidone.

6. The process of claim 5, wherein the esterification is carried out in the presence of N,N-dimethylacetamide or 1-methyl-2-pyrrolidone.

7. The process of claim 1, wherein the ascorbic acid is used in up to 25% by weight excess.

8. The process of claim 1, wherein the esterification is carried out at temperatures of about $-20°$ C. to about 40° C.

9. The process of claim 1, wherein the esterification also takes place in the presence of an inert solvent.

10. The process of claim 9, wherein the inert solvent is methylene chloride, chloroform, tetrahydrofuran, dioxan or acetonitrile.

11. The process of claim 9, wherein the volume ratio of N,N-dialkyl-alkanecarboxylic acid amide of formula I or cyclic amide of formula II to the inert solvent is from about 1:0.1 to about 1:1.

12. The process of claim 1, wherein the molar ratio of ascorbic acid to hydrogen halide is from about 1:0.1 to about 1:2.

13. The process of claim 12, wherein the hydrogen halide is hydrogen chloride.

14. The process of claim 3, wherein the 6-ascorbyl palmitate obtained from the resulting reaction mixture of esterification is isolated by diluting the reaction mixture with water and diethyl ether, diisopropyl ether, ethyl acetate or isobutyl methyl ketone, and filtering off the resulting 6-ascorbyl palmitate in crystalline form from the diluted reaction mixture.

* * * * *